(12) United States Patent
Perera et al.

(10) Patent No.: US 11,257,592 B2
(45) Date of Patent: Feb. 22, 2022

(54) ARCHITECTURE FOR MACHINE LEARNING MODEL TO LEVERAGE HIERARCHICAL SEMANTICS BETWEEN MEDICAL CONCEPTS IN DICTIONARIES

(71) Applicant: International Business Machines Corporation, Armonk, NY (US)

(72) Inventors: Pathirage D. S. U Perera, San Jose, CA (US); Cartic Ramakrishnan, San Jose, CA (US); Sheng Hua Bao, San Jose, CA (US); Ramani Routray, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 235 days.

(21) Appl. No.: 16/285,416

(22) Filed: Feb. 26, 2019

(65) Prior Publication Data
US 2020/0273573 A1    Aug. 27, 2020

(51) Int. Cl.
*G16H 50/20*    (2018.01)
*G16H 10/60*    (2018.01)
*G06N 20/00*    (2019.01)

(52) U.S. Cl.
CPC ............ *G16H 50/20* (2018.01); *G06N 20/00* (2019.01); *G16H 10/60* (2018.01)

(58) Field of Classification Search
None
See application file for complete search history.

(56) References Cited

U.S. PATENT DOCUMENTS

| | | | |
|---|---|---|---|
| 7,233,938 B2 | 6/2007 | Carus et al. | |
| 7,493,253 B1 | 2/2009 | Ceusters et al. | |
| 10,140,421 B1 * | 11/2018 | Bernard | A61B 8/565 |

(Continued)

OTHER PUBLICATIONS

S. Perera, "Optimizing Hierarchical Classification with Adaptive Node Collapses." Workshops at the Thirty-Second AAAI Conference on Artificial Intelligence, pp. 372-375. https://aaai.org/ocs/index.php/WS/AAAIW18/paper/view/16515.

(Continued)

*Primary Examiner* — Robert W Morgan
*Assistant Examiner* — Andrew E Lee
(74) *Attorney, Agent, or Firm* — Edell, Shapiro & Finnan, LLC

(57) ABSTRACT

A method, a system, and a computer program product are provided. A machine learning model is generated to process adverse event information and produce multiple corresponding medical codes associated with the adverse event information, wherein the multiple medical codes are semantically and hierarchically related in a medical taxonomy. The machine learning model includes multiple parallel output layers, each of which is associated with a corresponding medical code. The machine learning model is trained with training data elements, each of which includes adverse event information mapped to respective multiple medical codes, wherein results from each of the output layers adjusts the machine learning model. After completing the training, information pertaining to an adverse event is applied to the machine learning model to determine the corresponding multiple medical codes within the medical taxonomy.

17 Claims, 4 Drawing Sheets

(56) References Cited

U.S. PATENT DOCUMENTS

| | | | | |
|---|---|---|---|---|
| 2013/0226616 | A1* | 8/2013 | Nigam | G06Q 10/00 |
| | | | | 705/3 |
| 2015/0356647 | A1 | 12/2015 | Reiser et al. | |
| 2018/0060513 | A1* | 3/2018 | Tang | G16H 40/63 |
| 2019/0019582 | A1* | 1/2019 | Wallis | G06N 3/08 |
| 2019/0027235 | A1* | 1/2019 | Ferrandez-Escamez | |
| | | | | G06Q 20/14 |
| 2019/0034475 | A1* | 1/2019 | Parikh | G06N 20/20 |
| 2019/0244107 | A1* | 8/2019 | Murez | G06K 9/00791 |
| 2019/0272907 | A1* | 9/2019 | Aldairy | G06F 40/279 |
| 2019/0304604 | A1* | 10/2019 | Kupersmith | G06F 16/903 |
| 2020/0027531 | A1* | 1/2020 | White | G06F 40/20 |
| 2020/0027567 | A1* | 1/2020 | Xie | G16H 20/10 |
| 2020/0118682 | A1* | 4/2020 | Villazon-Terrazas | G06N 3/08 |

OTHER PUBLICATIONS

M. Zorzi, 2017. "Mapping Free Text into MedDRA by Natural Language Processing: A Modular Approach in Designing and Evaluating Software Extensions." In Proceedings of the 8th ACM International Conference on Bioinformatics, Computational Biology,and Health Informatics (ACM-BCB '17). ACM, New York, pp. 27-35.
Z. Miftahutdinov, "Leveraging Deep Neural Networks and Semantic Similarity Measures for Medical Concept Normalisation in User Reviews." Computational Linguistics and Intellectual Technologies: Proceedings of the International Conference "Dialogue 2018," Moscow, May 30-Jun. 2, 2018, 11 pages.
M. Dupuch, 2012. "Automatic creation and refinement of the clusters of pharmacovigilance terms." In Proceedings of the 2nd ACM SIGHIT International Health Informatics Symposium (IHI '12). ACM, New York, pp. 181-190.
A. Rios, 2015. "Convoluntional neural networks for biomedical text classification: application in indexing biomedical articles." In Proceedings of the 6th ACM Conference on Bioinformatics, Computational Biology and Health Informatics (BCB '15). ACM, New York, pp. 258-267.
C. Helwe, 2017. "CCS Coding of Discharge Diagnoses via Deep Neural Networks." In Proceedings of the 2017 International Conference on Digital Health (DH '17). ACM, New York pp. 175-179.
R. Farkas, et al., 2008 "Automatic construction of rule-based ICD-9-CM coding systems" BMC bioinformatics 9.3 (2008): S10.
I. Goldstein, et al., 2007 "Three approaches to automatic assignment of ICD-9-CM codes to radiology reports." AMIA Annual Symposium Proceedings. vol. 2007. American Medical Informatics Association, 2007.
S. Pereira, et al., 2006. "Construction of a semi-automated ICD-10 coding help system to optimize medical and economic coding." MIE. 2006.
S. Pakhomov, et al., 2006. "Automating the assignment of diagnosis codes to patient encounters using example-based and machine learning techniques." Journal of the American Medic Informatics Association 13.5 (2006): 516-525.

* cited by examiner

ARCHITECTURE FOR MACHINE LEARNING MODEL TO LEVERAGE HIERARCHICAL SEMANTICS BETWEEN MEDICAL CONCEPTS IN DICTIONARIES

BACKGROUND

Technical Field

Present invention embodiments relate to generating and training a machine learning model having an architecture that leverages hierarchical semantics between medical concepts in dictionaries for harmonized medical coding. In particular, the present invention embodiments relate to training of a machine learning model for automatically classifying adverse event information into multiple medical codes such that each of the multiple medical codes are included in a different, but semantically related hierarchical level of a dictionary of medical concepts.

2. Discussion of the Related Art

Many processes in a healthcare domain include identification of medical concepts in healthcare data. A few examples include coding of adverse event information to a Medical Dictionary for Regulatory Activities (MedDRA) dictionary, coding of drug information to a World Health Organization Drug Dictionary (WHO-DD), and coding of medical condition information to an International Classification of Diseases, 10th Revision (ICD-10) dictionary.

Coding tasks are inherently difficult due to a richness and complexity of the healthcare domain. For example, MedDRA is a highly specific and rich hierarchical dictionary with five levels that characterize adverse events. The five levels, from root to leaf nodes, are System Organ Class, High Level Group Term, High Level Term, Preferred Term, and Lowest Level Term. A latest version of the MedDRA dictionary has over 70,000 lowest level terms and is used to map reported adverse events to a standard vocabulary to facilitate international sharing of regulatory information for medical products. Mapping of adverse events to medical codes of the MedDRA dictionary is a challenging task for human practitioners having pharma domain knowledge due to a large number of possible codes and fine-grained semantic differences between medical codes at a leaf node level.

Traditionally, coding tasks are carried out by highly trained experts in the healthcare domain. Recently, solutions were developed to automate the coding tasks. The solutions use different variations of string matching techniques, traditional learning-based techniques, rule-based techniques, information retrieval techniques, and knowledge-based techniques for finding appropriate codes for medical concepts. Complexity and diversity of the medical concepts are challenging for these recent solutions. For example, traditional methods for coding adverse event information to MedDRA dictionary terms omit coding a significant portion of the adverse event information.

SUMMARY

According to one embodiment of the present invention, a method of medical coding via machine learning is provided. A processor generates a machine learning model to process adverse event information and produce multiple corresponding medical codes associated with the adverse event information. The multiple medical codes are semantically and hierarchically related in a medical taxonomy. The machine learning model includes multiple parallel output layers, each of which is associated with a corresponding medical code. Via the processor, the machine learning model is trained with training data elements, each of which includes adverse event information mapped to respective multiple medical codes. Results from each of the output layers adjust the machine learning model. After completing the training, the processor applies information pertaining to an adverse event to the machine learning model to determine multiple corresponding medical codes within the medical taxonomy.

According to a second embodiment of the present invention, a system for medical coding via machine learning is provided. The system includes at least one processor and a memory connected to the at least one processor. The at least one processor is configured to generate a machine learning model to process adverse event information and produce multiple corresponding medical codes associated with the adverse event information. The multiple medical codes are semantically and hierarchically related in a medical taxonomy. The machine learning model includes multiple parallel output layers, each of which is associated with a corresponding medical code. The at least one processor is configured to train the machine learning model with training data elements, each of which includes adverse event information mapped to respective multiple medical codes. Results from each of the output layers adjusts the machine learning model. After completing the training, the at least one processor is further configured to apply information pertaining to an adverse event to the machine learning model to determine corresponding multiple medical codes within the medical taxonomy.

In a third embodiment of the present invention, a computer program product is provided. The computer program product includes at least one computer readable storage medium having computer readable program code embodied therewith for execution on at least one processor of a computing device. The computer readable program code is configured to be executed by the at least one processor to perform a number of steps. According to the steps, a machine learning model is generated to process adverse event information and produce multiple corresponding medical codes associated with the adverse event information, wherein the multiple medical codes are semantically and hierarchically related in a medical taxonomy. The machine learning model includes multiple parallel output layers, each of which is associated with a respective corresponding medical code. The machine learning model is trained with training data elements, each of which includes adverse event information mapped to respective multiple medical codes. Results from each of the output layers adjust the machine learning model. After completing the training, information pertaining to an adverse event is applied to the machine learning model to determine corresponding multiple medical codes within the medical taxonomy.

BRIEF DESCRIPTION OF THE DRAWINGS

Generally, like reference numerals in the various figures are utilized to designate like components.

DETAILED DESCRIPTION

In various embodiments, a machine learning model is trained for performing medical coding tasks. The machine learning model exploits semantic similarity between medical information and medical codes at different hierarchical levels of a dictionary. The machine learning model is trained to simultaneously predict two medical codes having complementary semantic meaning, thereby increasing medical code prediction accuracy. In the various embodiments, the machine learning model may be a convolutional neural network.

In some embodiments, each item of medical information may be assigned to two medical codes, a first medical code on a leaf node and a second medical code on a parent node of the leaf node. Because the medical codes have similar semantic meaning and differ only in a level of granularity with respect to their description, simultaneous assignment of the two medical codes complement each other. As a result, effectiveness of training data is increased because each item of training data may be used twice during training. Further, due to increased use of the training data and extra guidance provided as a result of assigning a leaf node through its parent node, medical coding accuracy is increased.

Figure 1:
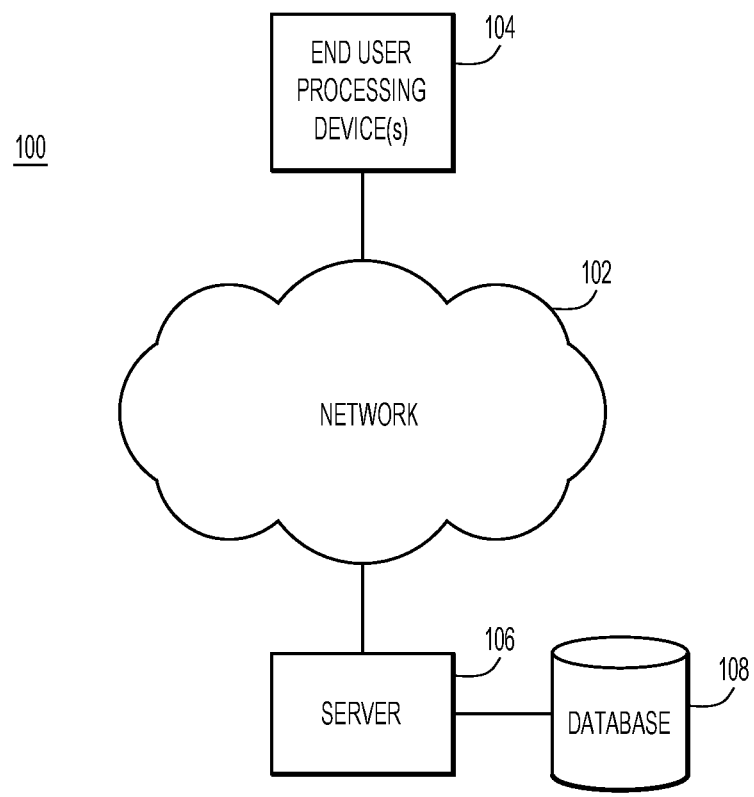
FIG. 1 shows an example operating environment according to embodiments of the invention.

An example environment 100 for use with present invention embodiments is illustrated in FIG. 1. Specifically, environment 100 may include one or more end user processing devices 104 and a server 106 connected to a network 102 either via a wired or a wireless connection. Server 106 further may be connected to a database 108, which may include a training set of data for training a machine learning model. In some embodiments, server 106 may include a server farm.

In some embodiments, instead of being connected to server 106, database 108 may be connected with a database server (not shown), which further may be connected to network 102.

End user processing device(s) 104 and server 106 may be remotely located from each other and may communicate via network 102. Network 102 may be implemented by any number of any suitable communications media (e.g., wide area network (WAN), local area network (LAN), Internet, Intranet, etc.). Alternatively, end user processing device(s) 104 and server 106 may be local to each other, and may communicate via any appropriate local communication medium (e.g., local area network (LAN), hardwire, wireless link, Intranet, etc.). In a standalone embodiment, end user processing device 104 may train the machine learning model using the training set of data and, after completing the training, may apply the machine learning model to recommend medical codes to assign to items of adverse event information.

End user processing device(s) 104 may be a handheld computing device, a tablet computer, a smartphone, a laptop computing device, a desktop computing device, or other type of computing device.

Server 106 may include a laptop computing device, a desktop computing device, a tablet computing device, or other type of computing device.

In some embodiments, after the machine learning model is trained, end user processing device(s) 104 may provide one or more items of adverse event information (e.g., natural language, verbatim, etc.) to server 106, which may include the machine learning model. Server 106 may apply the one or more items of adverse event information to the trained machine learning model to assign medical codes to each of the one or more items of adverse event information, which may be returned to each of end user processing device(s) 104 from which the one or more items of adverse event information originated. Alternatively, end user processing device(s) 104 may use a trained machine learning model residing thereon to assign the medical codes to each of the one or more items of adverse event information.

Figure 2:
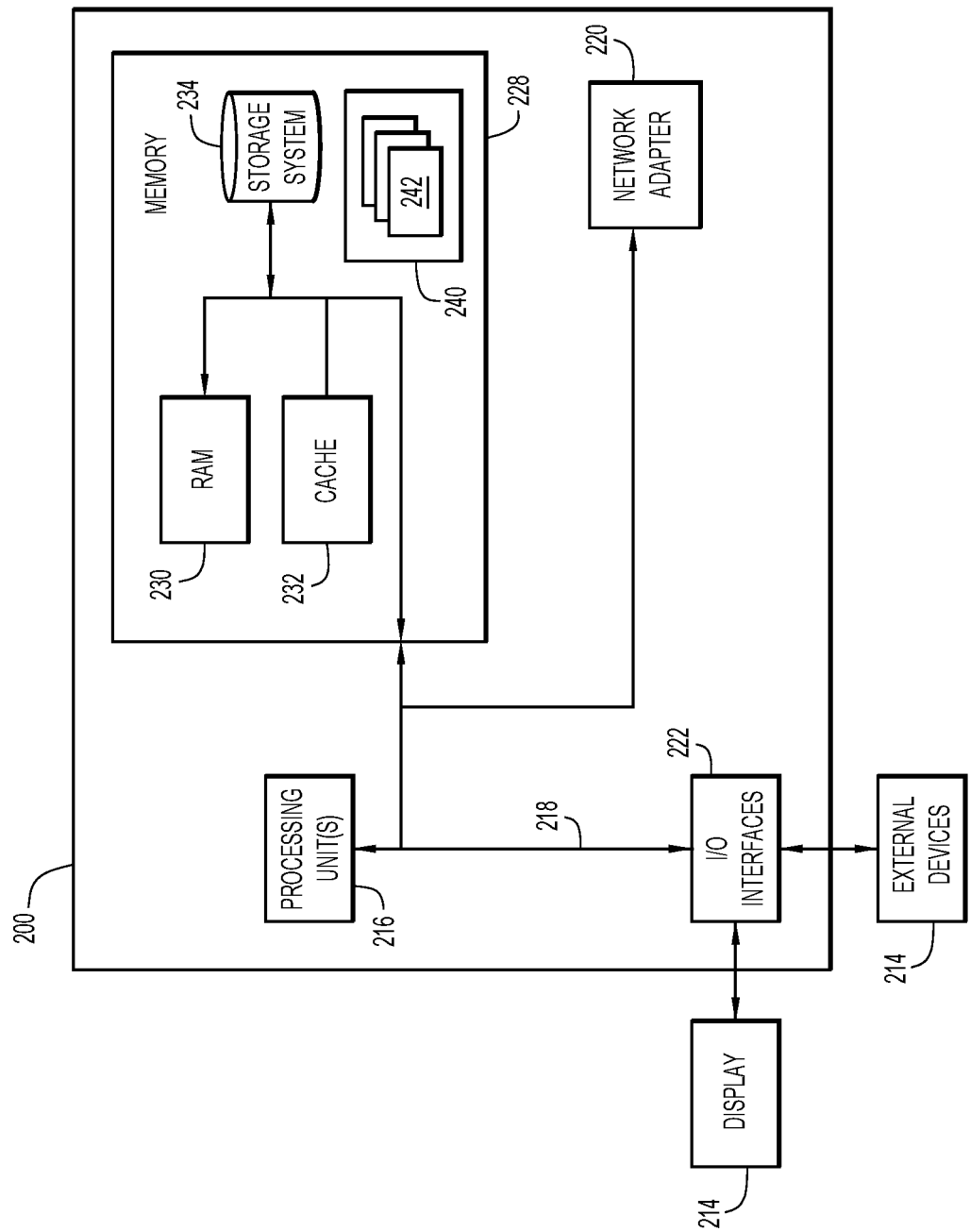
FIG. 2 is a functional block diagram of a general purpose computer for implementing embodiments of the invention.

Referring now to FIG. 2, a schematic of an example computer system 200 is shown, which may implement end user processing device 104 or server 106 in various embodiments. Computer system 200 is shown in a form of a general-purpose computing device. Components of computer system 200 may include, but are not limited to, one or more processors or processing units 216, a system memory 228, and a bus 218 that couples various system components including system memory 228 to one or more processing units 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 200 may include a variety of computer system readable media. Such media may be any available media that is accessible by computer system 200, and may include both volatile and non-volatile media, removable and non-removable media.

System memory 228 can include computer system readable media in the form of volatile memory, such as random access memory (RAM) 230 and/or cache memory 232. Computer system 200 may further include other removable/non-removable, volatile/non-volatile computer system storage media. By way of example only, storage system 234 can be provided for reading from and writing to a non-removable, non-volatile magnetic medium (not shown, which may include a "hard drive" or a Secure Digital (SD) card). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computer system 200 may also communicate with one or more external devices 214 such as a keyboard, a pointing device, one or more displays 224, one or more devices that enable a user to interact with computer system 200, and/or any devices (e.g., network card, modem, etc.) that enable computer system 200 to communicate with one or more other computing devices. Such communication can occur via Input/Output (I/O) interfaces 222. Still yet, computer system 200 can communicate with one or more networks such as a local area network (LAN), a general wide area network (WAN), and/or a public network (e.g., the Internet) via network adapter 220. As depicted, network adapter 220 communicates with the other components of computer system 200 via bus 218. It should be understood that, although not shown, other hardware and/or software components could be used in conjunction with computer system 200. Examples, include, but are not limited to: a microphone, one or more speakers, microcode, device drivers, redundant processing units, external disk drive arrays, RAID systems, tape drives, and data archival storage systems, etc.

Figure 3:
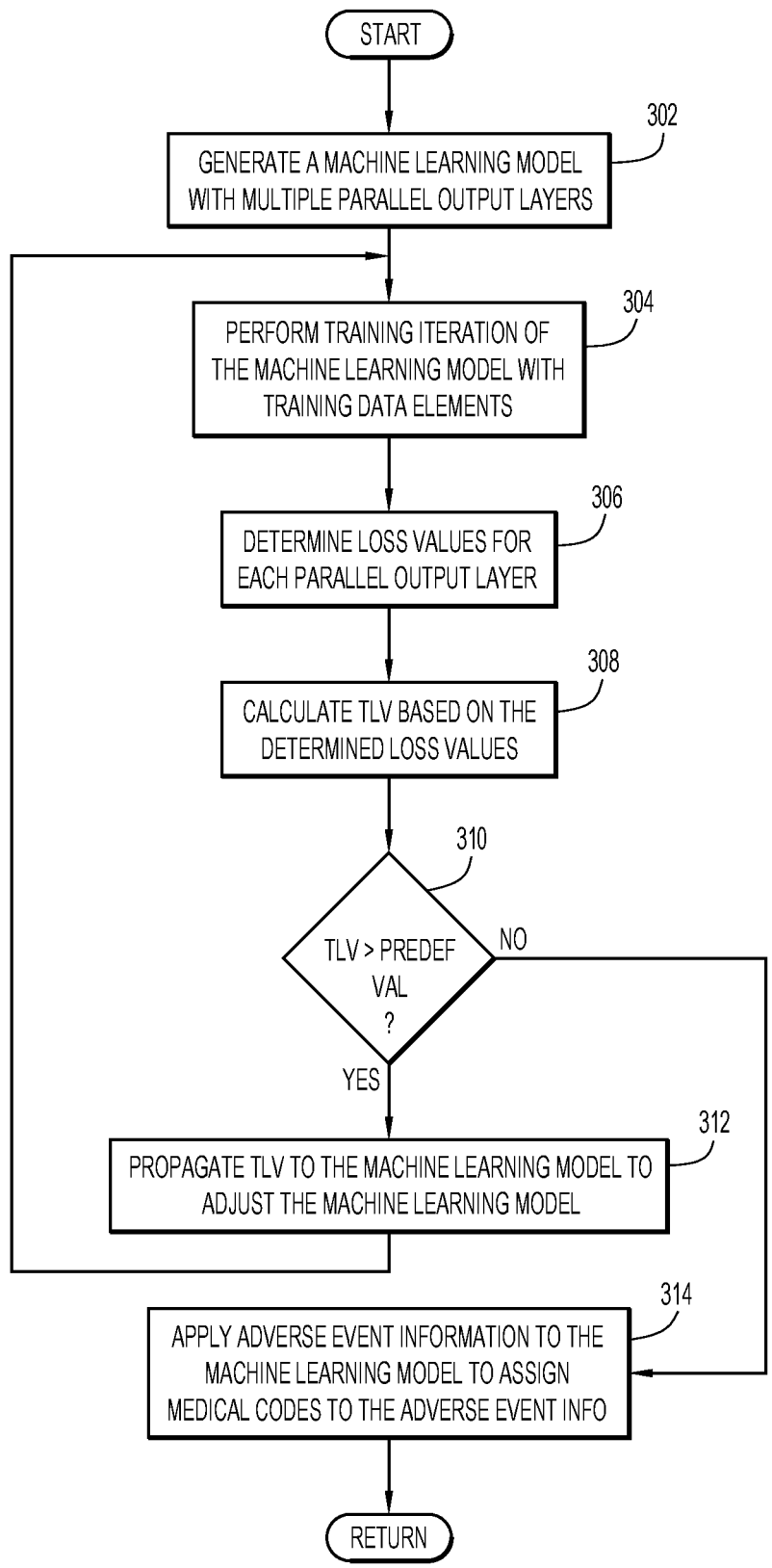
FIG. 3 is a flowchart illustrating an example process that may be performed according to various embodiments to train and use a machine learning model according to embodiments of the invention.

FIG. 3 is a flowchart that illustrates an example process that may be performed in a computing device such as, for example, end user processing device 104 or server 106 according to embodiments of the invention. The process may begin by generating a machine learning model with multiple parallel output layers (act 302). Each of the multiple parallel output layers is for predicting a medical code for an item of adverse event information having a complementary semantic meaning with respect to each medical code predicted by one or more other parallel output layers. In one embodiment, the multiple parallel output layers may include two parallel output layers, one of which may predict a medical code corresponding to a leaf node in a hierarchy and another of which predicts a medical code corresponding to a parent node of the leaf node in the hierarchy.

Next, the process may perform a training iteration of the machine learning model using training data elements (act 304). The training data elements may include items of adverse event information, each of which further includes corresponding multiple correct medical codes having similar semantic meanings and corresponding to different hierarchical levels of a medical taxonomy.

Next, the process may determine, for each of the multiple output layers, an error, or loss value, based on a predicted medical code and a correct medical code from the training data elements (act 306). The process then may calculate a total loss value based on the determined loss values for each of the multiple output layers (act 308). For example, in some embodiments, the total loss value may be calculated by summing the loss value from each of the parallel output layers.

If, during act 310, the calculated total loss value is determined to be greater than a predefined value, which indicates a desired level of accuracy for the machine learning model, then the total loss value may be provided to the machine learning model via backpropagation to adjust parameters of the machine learning model in order to improve prediction accuracy (act 312). Acts 304-310 then may be repeated.

If, during act 310, the total loss value is determined not to be greater than the predefined value, then a desired level of prediction accuracy has been achieved, training may be stopped and items of adverse event information may be applied to the machine learning model to assign medical codes to each of the items of adverse event information within the desired level of prediction accuracy (act 314).

In some embodiments, the machine learning model may be a convolutional neural network. According to one embodiment, the machine learning model may include two parallel output layers. Based on adverse event information, a first output layer of this embodiment may predict a medical code at a Lower Level Term (LLT) level of the MedDRA dictionary and a second output layer of this embodiment may predict a medical code at a Preferred Term (PT) level of the MedDRA dictionary. Each of the output layers may output a respective vector having a corresponding element for each possible medical code. Therefore, for this embodiment, the first output layer may store for each element of the respective vector a value between 0 and 1, which is an estimated probability that a medical code of the LLT level, corresponding to the element of the respective vector, is a correct medical code. Similarly, for this embodiment, the second output layer may store for each element of the respective vector an estimated probability that a medical code of the PT level, corresponding to the element of the vector, is a correct medical code. The machine learning model may predict, for each respective vector corresponding to the respective parallel output layer, a medical code corresponding to an element of the respective vector having a highest estimated probability value.

One common loss function that may be used in various embodiments to calculate a loss value for predicting a code during training is a cross entropy error. The loss value as defined according to cross entropy error is $-\Sigma c=1^M \, y_{o,c} \ln(p_{o,c})$, where M is a number of codes, ln is a natural log, $y_{o,c}$ is an actual probability that observation o is correctly assigned to medical code c and $p_{o,c}$ is a predicted probability (according to the machine learning model) that observation o is correctly assigned to medical code c.

For example, in an embodiment in which a LLT level medical code and a PT level medical code from the MedDRA dictionary are predicted based on an item of adverse event information. Values of each element of a respective vector for each of two parallel output layers correspond to an estimated probability that a corresponding medical code of a corresponding level of the MedDRA dictionary is a correct medical code. During training, the correct medical codes at the LLT level and the PT level are known. A respective vector representing actual probabilities for medical codes corresponding to the LLT level or the PT level has a value of zero for all elements of the respective vector corresponding to incorrect medical codes and a value of one for an element of the respective vector corresponding to a correct medical code. For the sake of providing a simple example loss value calculation according to the cross entropy error, assume that an output layer has five possible codes, and a third possible code is a correct code corresponding to a training item of adverse event information, then a vector of actual probabilities of a corresponding code being correct would be (0, 0, 1, 0, 0). If the machine learning model produced a vector of estimated probabilities having values (0.324, 0.216, 0.802, 0.137, 0.112), then the loss value for this particular example would be $-((0)+(0)+(1 \times \ln(0.802))+(0)+(0))$, which is 0.2206467.

Assuming that during a training iteration the machine learning model produces estimated probabilities for predicting a code for each of many items of adverse event information, a respective loss value for each predicted code corresponding to a respective item of adverse information may be calculated according to the formula described above. A loss value for an output layer may be calculated by summing the respective loss values with respect to each respective item of adverse information. Further, a total loss value for the output layers may be calculated by summing the loss value for each of the output layers.

In other embodiments, a different loss function may be used.

According to various embodiments, each training instance produces multiple loss values, one for each parallel output layer, which may be propagated back to the machine learning model via backpropagation. Given that each of the parallel output layers have a hierarchical semantic relationship with one or more other parallel output layers, loss values for each output layer complement loss values of the one or more other output layers and allow the machine learning model to adjust in a same direction for each of the output layers. In other words, for each of the output layers, the machine learning model is pushed, or adjusted, in a same direction to decrease the loss value for each of the parallel output layers.

In order to train a machine learning model to assign a medical code to an item of adverse event information, each word of items of adverse event information may be assigned to respective multidimensional vectors. In some embodiments, each unique word of the items of adverse event information may be assigned to an n-dimensional vector, where n may be 300, 500, 1,000, or another suitable value.

Word2vec and Global Vectors (GloVe) for word representation are two known method for assigning words to multidimensional vectors. Using either method results in multidimensional vectors corresponding to words, wherein words that share common contexts in a large corpus correspond to multidimensional vectors that are located in close proximity to one another in a vector space.

In other embodiments, other methods may be used to assign words to multidimensional vectors. For example, characters such as letters "a" through "z", numbers "0" through "9" and other characters may each be assigned to a unique multidimensional vector. Further, each word also may be assigned to a unique multidimensional vector. In these other embodiments, each word of an item of adverse event information may be represented by a combination of the multidimensional vectors corresponding to each character of the word and the multidimensional vector corresponding to the word.

In yet other embodiments, each unique word of the adverse event information of may be assigned to a corresponding n-dimensional vector based on other methods. Any of a number of known methods may be used to assign a corresponding unique multidimensional vector to each of the unique words.

Figure 4:
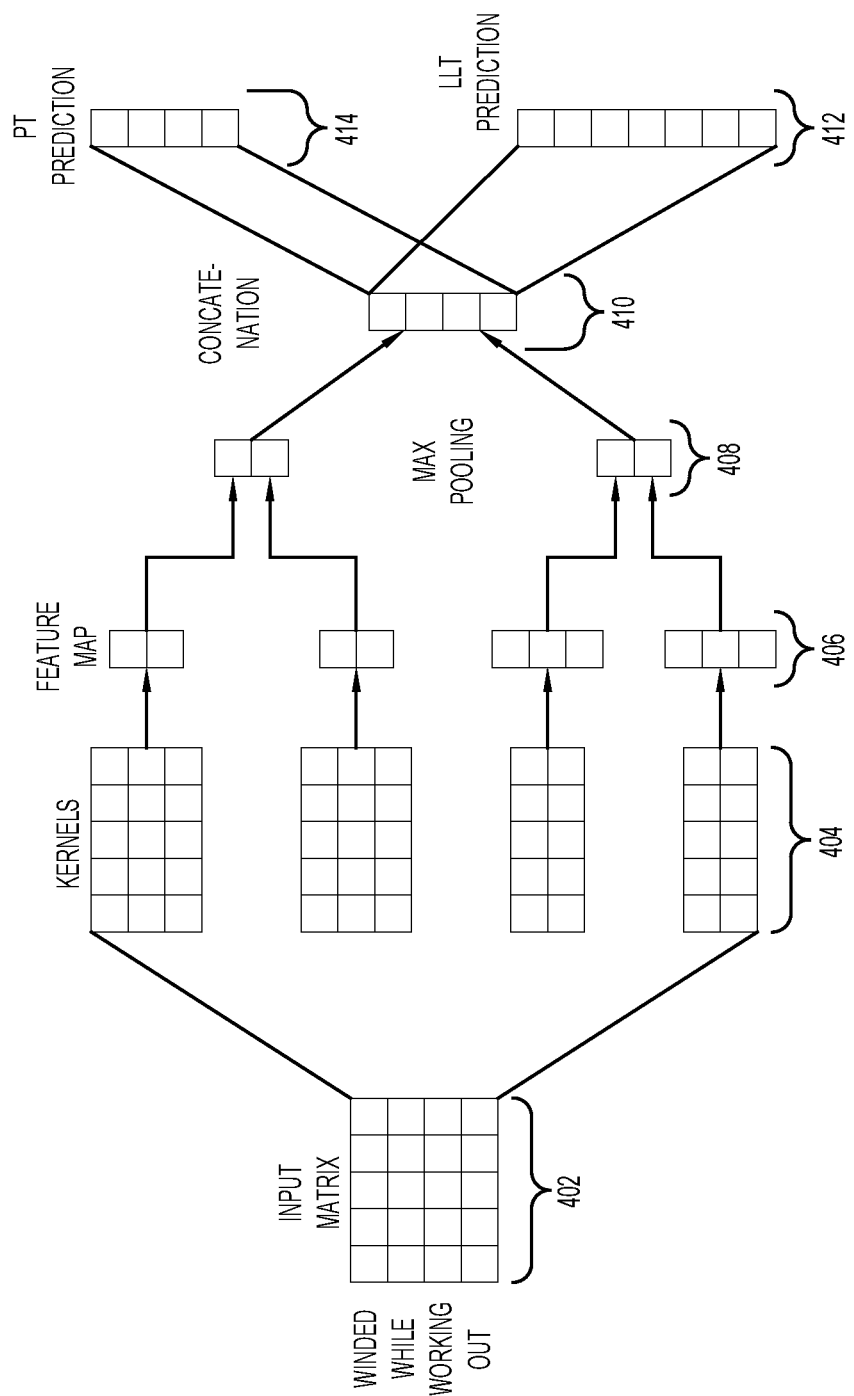
FIG. 4 shows an example convolutional neural network that may implement a machine learning model according to various embodiments.

FIG. 4 illustrates an example structure of a convolutional neural network for a machine learning model for assigning a PT level medical code and a LLT medical code of the MedDRA dictionary to an item of adverse event information.

Each row of an input matrix 402 may include a multidimensional vector representation of a word of adverse event information such as, for example, "winded while working out" or another item of adverse event information. Multiple kernels 404 of different sizes may be applied to input matrix 402 to produce feature maps. Although, FIG. 4 shows four kernels 404, some embodiments may include 128 kernels or another number of kernels. Typically, each kernel may have of a size of 2 or 3 rows, but could be another size in other embodiments. In FIG. 4, a top two kernels may have three rows, which may be applied to a sliding window of three word vectors. A top three word vectors, corresponding to, for example, "winded while working", may be applied to a top kernel 404 to produce one output of a feature map and a bottom three word vectors, corresponding to, for example, "while working out" may be applied to top kernel 404 to produce a second output of the feature map. For example, values of columns of "winded", in the input matrix, may be multiplied by corresponding column values of a top row of top kernel 404 and summed, values of columns of "while", in the input matrix, may be multiplied by corresponding column values of a middle row of top kernel 404 and summed, and values of columns of "working", in the input matrix, may be multiplied by corresponding column values of a bottom row of top kernel 404 and summed. The sums of the products produced for each row may then be summed to produce a top row of a feature map 406. Similarly, values of columns of "while", in the input matrix, may be multiplied by corresponding column values of a top row of top kernel 404 and summed, values of columns of "working", in the input matrix, may be multiplied by corresponding column values of a middle row of top kernel 404 and summed, and values of columns of "out", in the input matrix, may be multiplied by corresponding column values of a bottom row of top kernel 404 and summed. The sums of the products produced for each row may then be summed to produce a bottom row of feature map 406.

Similarly, the top three word vectors may be applied to a second kernel 404 (second kernel from the top) to produce one output of a second feature map 406 and a bottom three word vectors may be applied to the second kernel 404 to produce a second output of the second feature map 406.

In a similar manner, a third kernel 404 may be applied to the first two word vectors of input matrix 402 to produce a first output of a third feature map 406. The third kernel 404 may be applied to the second and third word vectors of input matrix 402 to produce a second output of the third feature map 406, and the third kernel 404 may be applied to the third and fourth word vectors of input matrix 402 to produce a third, or bottom, output of the third feature map 406.

A fourth kernel 404 may be applied to the word vectors of input matrix 402 in a same manner as the third kernel to produce three outputs of a fourth feature map 406.

Next, max pooling may be performed on the feature maps to reduce a spatial size of a representation of the feature maps. For example, a larger value from top feature map 406 may be placed in a top row of top max pool 408 and a larger value from second feature map 406 may be placed in a bottom row of top max pool 408. A largest value from third feature map 406 may be placed in a top row of second max pool 408 and a largest value from fourth feature map 406 may be placed in a bottom row of second max pool 408.

Next, max pools 408 may be concatenated to produce a concatenated result 410, which may be applied to each of two parallel fully connected output layers to produce a respective multidimensional vector such that each element of a first multidimensional vector 412 corresponds to a different LLT level medical code and each element of a second multidimensional vector 414 corresponds to a different PT level medical code and the value of each of the elements is between 0 and 1, inclusive and corresponds to an estimated probability that a corresponding medical code is a correct medical code based on past observations. A latest version of the MedDRA dictionary has over 70,000 medical codes at the LLT level. Therefore, a corresponding multidimensional vector for predicting a LLT medical code at the output layer may have a same number of dimensions. Similarly, a latest version of the MedDRA dictionary has over 20,000 medical codes at the PT level. Therefore, a corresponding multidimensional vector for predicting a PT level medical code at the output layer may have a same number of dimensions.

The above-mentioned deep learning-based embodiments for medical coding of adverse event information exploits semantic similarity among medical codes at different hierarchical levels of a medical taxonomy. Simultaneous prediction of multiple medical codes having complementary semantic meanings results in increased coding accuracy. For example, in an embodiment that predicts medical codes at the LLT level and the PT level of the MedDRA dictionary, each item of adverse event information is assigned to two medical codes, a medical code of a leaf node of the hierarchy and a medical code of a parent node of the leaf node. Because both codes have similar semantic meaning and differ only in a granularity level of their description, the simultaneous assignment of the two medical codes complement each other to thereby increase effectiveness of training data.

It will be appreciated that the embodiments described above and illustrated in the drawings represent only a few of the many ways of implementing embodiments for training a machine learning model to assign medical codes to respective items of adverse event information.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be included within or coupled to a server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method of medical coding via machine learning comprising:
   generating, via a processor, a machine learning model to process adverse event information and produce a plurality of corresponding medical codes associated with the adverse event information, wherein the plurality of medical codes are semantically and hierarchically related in a medical taxonomy, and the machine learning model includes a plurality of parallel output layers each associated with and trained to produce a corresponding medical code of a different level of the medical taxonomy, and wherein the plurality of parallel output layers includes a first parallel output layer with a plurality of first result elements each assigned to a medical code of a child node of the medical taxonomy and a second parallel output layer with a plurality of second result elements each assigned to a medical code of a parent node of the medical taxonomy corresponding to the child node of the first parallel output layer;
   training, via the processor, the machine learning model with training data elements each including adverse event information mapped to a respective plurality of medical codes of child and parent nodes of the medical taxonomy, wherein results from each of the parallel output layers are used to determine an error value for that parallel output layer to adjust the machine learning model, and wherein an error value for the first parallel output layer is based on the results of the first parallel output layer and a mapped medical code of a training data element for the child node associated with the first parallel output layer and an error value for the second parallel output layer is based on the results of the second parallel output layer and a mapped medical code of the training data element for the parent node associated with the second parallel output layer; and
   applying, via the processor after completing the training, information pertaining to an adverse event to the machine learning model to determine a plurality of corresponding medical codes within the medical taxonomy including a medical code from each of the child and parent nodes associated with the first and second parallel output layers.

2. The method of claim 1, wherein the machine learning model comprises a neural network.

3. The method of claim 2, wherein the neural network comprises:
   an input layer to provide adverse event information;
   a convolutional layer including a plurality of kernels to identify features of the adverse event information of the input layer; and
   the plurality of parallel output layers each coupled to the convolutional layer to determine the corresponding medical code.

4. The method of claim 3, wherein outputs from the plurality of kernels of the convolutional layer are pooled and concatenated for processing by the plurality of parallel output layers.

5. The method of claim 1, wherein the medical taxonomy includes a Medical Dictionary for Regulatory Activities (MedDRA) dictionary, and the plurality of parallel output layers are associated with MedDRA codes including a preferred term code and a lowest level term code.

6. The method of claim 1, wherein the training of the machine learning model further comprises:
   performing a training iteration of the machine learning model with the training data elements;
   determining, after the performing of the training iteration, a first loss value at the first parallel output layer and a second loss value at the second parallel output layer;
   calculating a total loss value based on the first loss value and the second loss value;
   repeating, while the total loss value is greater than a predefined value:
      propagating the total loss value to the machine learning model via backpropagation to adjust the machine learning model, and
      repeating the performing of the training iteration, the determining of the first loss value and the second loss value, and the calculating of the total loss value based on the first loss value and the second loss value.

7. A system for medical coding via machine learning, the system comprising:
   at least one processor; and
   a memory connected to the at least one processor, wherein the at least one processor is configured to:
      generate a machine learning model to process adverse event information and produce a plurality of corresponding medical codes associated with the adverse event information, wherein the plurality of medical codes are semantically and hierarchically related in a medical taxonomy, and the machine learning model includes a plurality of parallel output layers each associated with and trained to produce a corresponding medical code of a different level of the medical taxonomy, and wherein the plurality of parallel output layers includes a first parallel output layer with a plurality of first result elements each assigned to a medical code of a child node of the medical taxonomy and a second parallel output layer with a plurality of second result elements each assigned to a medical code of a parent node of the medical taxonomy corresponding to the child node of the first parallel output layer;
      train the machine learning model with training data elements each including adverse event information mapped to a respective plurality of medical codes of child and parent nodes of the medical taxonomy, wherein results from each of the parallel output layers are used to determine an error value for that parallel output layer to adjust the machine learning model, and wherein an error value for the first parallel output layer is based on the results of the first parallel output layer and a mapped medical code of a training data element for the child node associated with the first parallel output layer and an error value for the second parallel output layer is based on the results of the second parallel output layer and a mapped medical code of the training data element for the parent node associated with the second parallel output layer; and apply, after completing the training, information pertaining to an adverse event to the machine learning model to determine a plurality of corresponding medical codes within the medical taxonomy including a medical code from each of the child and parent nodes associated with the first and second parallel output layers.

8. The system of claim 7, wherein the machine learning model comprises a neural network.

9. The system of claim 8, wherein the neural network comprises:
    an input layer to provide adverse event information;
    a convolutional layer including a plurality of kernels to identify features of the adverse event information of the input layer; and
    the plurality of parallel output layers each coupled to the convolutional layer to determine the corresponding medical code.

10. The system of claim 9, wherein outputs from the plurality of kernels of the convolutional layer are pooled and concatenated for processing by the plurality of parallel output layers.

11. The system of claim 7, wherein the medical taxonomy includes a Medical Dictionary for Regulatory Activities (MedDRA) dictionary, and the plurality of parallel output layers are associated with MedDRA codes including a preferred term code and a lowest level term code.

12. The system of claim 7, wherein the at least one processor being configured to train the machine learning model with the training data elements further comprises the at least one processor being configured to:
    perform a training iteration of the machine learning model with the training data elements;
    determine, after the performing of the training iteration, a first loss value at the first parallel output layer and a second loss value at the second parallel output layer;
    calculate a total loss value based on the first loss value and the second loss value; and
    repeat, while the total loss value is greater than a predefined value:
        propagate the total loss value to the machine learning model via backpropagation to adjust the machine learning model, and
        repeat the performing of the training iteration, the determining of the first loss value and the second loss value, and the calculating of the total loss value based on the first loss value and the second loss value.

13. A computer program product comprising at least one computer readable storage medium having computer readable program code embodied therewith for execution on at least one processor of a computing device, the computer readable program code being configured to be executed by the at least one processor to perform:
    generating a machine learning model to process adverse event information and produce a plurality of corresponding medical codes associated with the adverse event information, wherein the plurality of medical codes are semantically and hierarchically related in a medical taxonomy, and the machine learning model includes a plurality of parallel output layers each associated with and trained to produce a corresponding medical code of a different level of the medical taxonomy, and wherein the plurality of parallel output layers includes a first parallel output layer with a plurality of first result elements each assigned to a medical code of a child node of the medical taxonomy and a second parallel output layer with a plurality of second result elements each assigned to a medical code of a parent node of the medical taxonomy corresponding to the child node of the first parallel output layer;
    training the machine learning model with training data elements each including adverse event information mapped to a respective plurality of medical codes of child and parent nodes of the medical taxonomy, wherein results from each of the parallel output layers are used to determine an error value for that parallel output layer to adjust the machine learning model, and wherein an error value for the first parallel output layer is based on the results of the first parallel output layer and a mapped medical code of a training data element for the child node associated with the first parallel output layer and an error value for the second parallel output layer is based on the results of the second parallel output layer and a mapped medical code of the training data element for the parent node associated with the second parallel output layer; and
    applying, after completing the training, information pertaining to an adverse event to the machine learning model to determine a plurality of corresponding medical codes within the medical taxonomy including a medical code from each of the child and parent nodes associated with the first and second parallel output layers.

14. The computer program product of claim 13, wherein:
    the machine learning model comprises a neural network; and
    the neural network comprises:
        an input layer to provide adverse event information;
        a convolutional layer including a plurality of kernels to identify features of the adverse event information of the input layer; and
        the plurality of parallel output layers each coupled to the convolutional layer to determine the corresponding medical code.

15. The computer program product of claim 14, wherein outputs from the plurality of kernels of the convolutional layer are pooled and concatenated for processing by the plurality of parallel output layers.

16. The computer program product of claim 13, wherein the medical taxonomy includes a Medical Dictionary for Regulatory Activities (MedDRA) dictionary, and the plurality of parallel output layers are associated with MedDRA codes including a preferred term code and a lowest level term code.

17. The computer program product of claim 13, wherein the computer readable program code being configured to train the machine learning model with the training data elements further comprises the computer readable program code being configured to:
    perform a training iteration of the machine learning model with the training data elements;
    determine, after the performing of the training iteration, a first loss value at the first parallel output layer and a second loss value at the second parallel output layer;
    calculate a total loss value based on the first loss value and the second loss value; and
    repeat, while the total loss value is greater than a predefined value:
        propagate the total loss value to the machine learning model via backpropagation to adjust the machine learning model, and
        repeat the performing of the training iteration, the determining of the first loss value and the second loss value, and the calculating of the total loss value based on the first loss value and the second loss value.

\* \* \* \* \*